United States Patent
Dunn et al.

(10) Patent No.: US 7,288,542 B2
(45) Date of Patent: Oct. 30, 2007

(54) NON-NUCLEOSIDE REVERSE TRANSCRIPTASE INHIBITORS

(75) Inventors: James Patrick Dunn, Los Altos, CA (US); Todd Richard Elworthy, Los Gatos, CA (US); Joan Heather Hogg, Sunnyvale, CA (US); Dimitrios Stefanidis, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 186 days.

(21) Appl. No.: 11/085,869

(22) Filed: Mar. 22, 2005

(65) Prior Publication Data

US 2005/0215554 A1    Sep. 29, 2005

Related U.S. Application Data

(60) Provisional application No. 60/555,798, filed on Mar. 23, 2004.

(51) Int. Cl.
A01N 43/58    (2006.01)
C07D 401/00   (2006.01)
C07D 403/00   (2006.01)

(52) U.S. Cl. .............. 514/247; 544/238; 544/239; 544/232; 514/850; 514/252.03; 514/252.05

(58) Field of Classification Search ........... 514/247, 514/85, 252.03, 252.05; 544/238, 239, 232
See application file for complete search history.

(56) References Cited

U.S. PATENT DOCUMENTS 5,886,178 A    3/1999   Allen et al.
2004/0198736 A1   10/2004   Dunn et al.

FOREIGN PATENT DOCUMENTS

| WO | WO96/24343 A1 | 8/1996 |
| WO | WO96/34851 A1 | 11/1996 |
| WO | WO97/02023 A1 | 1/1997 |
| WO | WO97/02024 A1 | 1/1997 |
| WO | WO 01/86570 A1 | 11/2001 |

OTHER PUBLICATIONS

West, Solid State Chemistry, 1988, pp. 358, 365.*
Vippagunta, et al., Advanced Drug Delivery Reviews 48: 3-26, 2001.*
Ulrich, Kirk-Othmer Encyclopedia of Chemical Technology, 2002.*
Moore, et al., Biochem. J. (1992) 288, 717-719.*
Marcus, et al., PubMed Abstract, 2002.*
van Heeswijk, et al., PubMed Abstract, 2001.*
, Miles, Medline abstract, 2005.*
Webster's Comprehensive Dictionary, 1996.*
De Clercq, Erik, "New Developments in Anti-HIV Chemotherapy," *Current Medicinal Chemistry*, 2001, pp. 1543-1572, vol. 8. No. 13.
Leeson, Paul D., "Selective Thyromimetics. Cardiac-Sparing Thyroid Hormone Analogues Containing 3'-Arylmethyl Substituents," *J. Med. Chem.*, 1989, pp. 320-336, vol. 32, No. 2.
H. Bundgaar, *Design of Prodrugs: Bioreversible derivatives for various functional groups and chemical entities in Design of Prodrugs*, H. Bundgaard (ed) Elsevier Science Publishers, Amersterdam 1985, pp. 10-27.
S. A. Varia et al., "Phenytoin Prodrugs III: Water soluble prodrugs for Oral and/or Parental Use," *J. Pharm. Sci.*, 1984 pp. 1068-1073, vol. 73:8.
Buckheit, Jr., Robert W., "Non-nucleoside reverse transcriptase inhibitors: perspectives on novel therapeutic compounds and strategies for the treatment of HIV infection," *Expert Opin. Investig. Drugs*, Ashley Publications Ltd., 2001, pp. 1423-1442, vol. 10, No. 8.

* cited by examiner

*Primary Examiner*—Mark Berch
*Assistant Examiner*—Cecilia Jaisle
(74) *Attorney, Agent, or Firm*—Brian L. Buckwalter

(57) ABSTRACT

The present invention relates to a compounds according to formula I, methods for treating diseases mediated by human immunodeficieny virus by administration of a compound according to formula I and pharmaceutical compositions for treating diseases mediated by human immunodeficieny virus containing a compound according to formula I where $R^1$, $R^2$, $R^3$, $R^4$, $R^5$, $R^6$, $R^7$ and $R^8$ are as defined herein

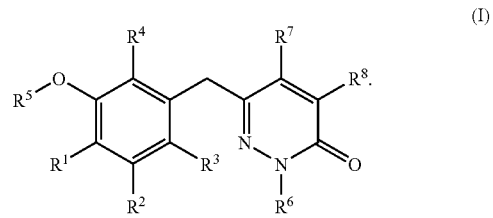

(I)

36 Claims, No Drawings

NON-NUCLEOSIDE REVERSE TRANSCRIPTASE INHIBITORS

CROSS REFERENCE TO RELATED APPLICATIONS

This application claims the benefit of priority to U.S. Ser. No. 60/555,798 filed Mar. 23, 2004, which is hereby incorporated by reference in its entirety.

FIELD OF THE INVENTION

The invention relates to the field of antiviral therapy and, in particular, to non-nucleoside reverse transcriptase inhibitors for treating Human Immunodeficiency Virus (HIV) mediated diseases. The invention provides novel pyridazinone compounds, pharmaceutical compositions comprising these compounds, methods for treatment or prophylaxis of HIV mediated diseases employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the $CD4^+$ T-cell, with attendant susceptibility to opportunistic infections. HIV infection is also associated with a precursor AIDs-related complex (ARC), a syndrome characterized by symptoms such as persistent generalized lymphadenopathy, fever and weight loss.

In common with other retroviruses, the HIV genome encodes protein precursors known as gag and gagpol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. Montaner et al. Antiretroviral therapy: "the state of the art", Biomed & Pharmacother. 1999 53:63-72; R. W. Shafer and D. A. Vuitton, *Highly active retroviral therapy (HAART) for the treatment of infection with human immunodeficiency virus type 1*, Biomed. & Pharmacother. 1999 53:73-86; E. De Clercq, *New Developments in Anti-HIV Chemotherap.* Curr. Med. Chem. 2001 8:1543-1572) Two general classes of RTI inhibitors have been identified: nucleoside reverse transcriptase inhibitors (NRTI) and non-nucleoside reverse transcriptase inhibitors (NNRTI).

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity. (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8)1423-1442; E. De Clercq *The role of non-nucleoside reverse transcriptase inhibitors (NNRTIs) in the therapy of HIV-1 infection*, Antiviral Res. 1998 38:153-179; G. Moyle, *The Emerging Roles of Non-Nucleoside Reverse Transcriptase Inhibitors in Antiviral Therapy*, Drugs 2001 61(1):19-26) Although over thirty structural classes of NNRTIs have been identified in the laboratory, only three compounds have been approved for HIV therapy: efavirenz, nevirapine and delavirdine. Although initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT.

While combination therapy with NRTIs, PIs and NNRTIs has, in many cases, dramatically lowered viral loads and slowed disease progression, significant therapeutic problems remain. The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

U.S. Publication No. 20040198736 (J. P. Dunn et al.) filed Mar. 23, 3004 discloses benzyl pyridazinone compounds that inhibit HIV reverse transcriptase, the use of benzyl pyridazinones to treat and prevent HIV infection and pharmaceutical compositions containing benzyl pyridazinones. U.S. Publication No. 20040192704 (J. P. Dunn et al.) filed Mar. 23, 2004 discloses benzylic heterocyclic compounds that inhibit HIV reverse transcriptase. Both applications are hereby incorporated by reference in their entirety. Benzyl-pyridazinone compounds have been extensively investigated as thyroxin analogs which can decrease plasma cholesterol without stimulating cardiac activity (A. H. Underwood et al. *A thyromimetic that decreases plasma cholesterol without increasing cardiovascular activity* Nature 1986 324(6096): 425-429; P. D. Leeson et al. *Selective thyromimetics. Cardiac-sparing thyroid hormone analogs containing 3'-arylmethyl substituents* J. Med Chem 1989 32(2):320-326; P. D. Leeson et al. EP 0188351). WO9624343 (D. J. Dunnington) discloses oxo-pyridazinylmethyl substituted tyrosines are selective antagonists for the hematopoietic phosphatase SH2 domain which may render them useful to increase erythropoiesis and haematopoiesis. WO 9702023 (D. J. Dunnington) and WO9702024 (D. J. Dunnington) further disclose these compounds are specific inhibitors of the human Stat 6 SH2 domain and may be useful for treating asthma, allergic rhinitis and anemia. WO2001085670 (H. Shiohara et al.) discloses related malonamide derivatives useful for treating circulatory diseases. EP 810218 (D. A. Allen et al.) discloses benzoyl substituted benzyl-pyridazinone compounds which are cyclooxygenase inhibitors and potential antiinflammatory or analgesic compounds. None of the references teaches therapy for HIV infections or inhibition of HIV reverse transcriptase.

Drug failure can produce selection pressure for the appearance of resistant strains. The facility which mutations occur during HIV replication require inhibitors that exhibit activity against a spectrum of enzymes with one or more point mutations. Since any compound's potency against a group of reverse transcriptases with one or more mutations is rarely uniform, a high circulating level of the active pharmaceutical ingredient is desireable to attempt to inhibit the least sensitive mutant RT. High circulating levels can suppress the emergence of new mutant strains. The pyridazinones (I) are frequently high-melting compounds with limited solubility. These properties are often associated with limited bioavailability.

Chemical derivatization of active drug moieties is frequently undertaken for a variety of reasons including modification of the physical properties of the active drug, optimization of the pharnacokinetic parameters and site-specific targeting or localization of the active moiety to specific target tissues or cells. Albert introduced the term "prodrug" to describe a compound which lacks intrinsic biological activity but which is capable of metabolic transformation to the active drug substance (A. Albert, *Selective Toxicity*, Chapman and Hall, London, 1951). While the metabolic transformation can catalyzed by specific enzymes, often hydrolases, the active compound can also be released by non-specific chemical processes. Produgs have been recently reviewed (P. Ettmayer et al., *J. Med Chem.* 2004 47(10):2393-2404; K. Beaumont et al., *Curr. Drug Metab.* 2003 4:461-485; H. Bundgaard, *Design of prodrugs: Bioreversible derivatives for various functional groups and chemical entities in Design of Prodrugs*, H. Bundgaard (ed) Elsevier Science Publishers, Amersterdam 1985).

Prodrugs used with amidese include Mannich bases 1, N-hydroxymethyl derivatives 2 (R"=H), N-acyloxy derivatives 2 (R"=C(=O)R'"), amides 4 and phosphates 3 (R=H, alkyl, cations). (H. Bundgaard supra, pp 10-27; S. A. Varia et al., *J. Pharm. Sci.*, 1984 73(8):1068-1073).

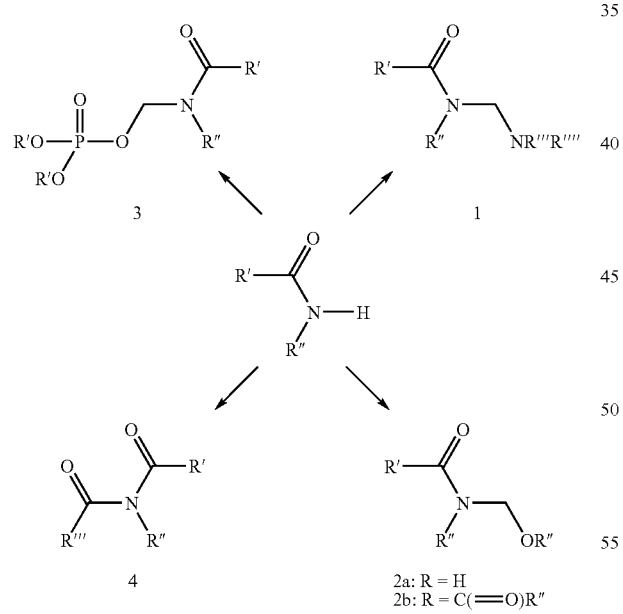

SUMMARY OF THE INVENTION

The present invention relates to a compounds according to formula I, methods for treating or preventing diseases mediated by human immunodeficieny virus or treating acquired immunodeficiency syndrome or AIDS related complex by administration of a compound according to formula I and pharmaceutical compositions for treating diseases mediated by human immunodeficiency virus containing a compound according to formula I,

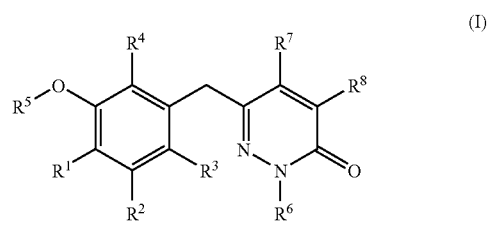

wherein;

$R^1$, $R^2$, $R^3$ and $R^4$ are each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ haloalkylthio, halogen, amino, alkylamino, dialkylamino, acylamino, nitro and cyano;

$R^5$ is aryl or heteroaryl radical said heteroaryl radical selected from the group consisting of pyridinyl, pyridine N-oxide, indole, indole N-oxide, quinoline, quinoline N-oxide, pyrimidinyl, pyrazinyl and pyrrolyl; wherein, said aryl and said heteroaryl radicals are optionally substituted with one to three substituents independently selected from the group consisting of $C_{1-6}$ alkyl, $C_{2-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, acylamino, acyl, $C_{1-6}$ alkoxycarbonyl, carbamoyl, $C_{1-6}$ N-alkylcarbamoyl, $C_{1-6}$ N,N-dialkylcarbamoyl, nitro and cyano;

$R^6$ is selected from the group consisting of $CH_2OH$, $CH_2CH_2OH$, $CH_2OC(=O)XR^9$, $CH_2CH_2OC(=O)XR^9$, $CH_2OCOCH(R^{13})NHR^{14}$, $CH_2CO_2R^{10}$, $CH_2NR^{11}R^{12}$, $CH_2OP(=O)(OH)_2$ and $CH(NR^{11}R^{12})CO_2R^{10}$;

$R^7$ and $R^8$ taken independently are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ alkylsulfonyl, halogen and N-morpholinyl;

$R^9$ is $C_{1-10}$ alkyl, $C_{1-10}$ heteroalkyl, $(CH_2)_oCO_2H$, $CH=CHCO_2H$, aryl, $(CH_2)_nNR^{11a}R^{12a}$ or heteroaryl said aryl and said heteroaryl optionally substituted with one to three substituents independently selected from the group consisting of $C_{1-6}$ alkyl, $C_{2-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkyl sulfonyl, $C_{1-6}$ haloalkyl, $C_{1-6}$ haloalkylthio, hydroxy, halogen, amino, $C_{1-6}$ alkylamino, $C_{1-6}$ dialkylamino, acylamino, acyl, $C_{1-6}$ alkoxycarbonyl, carbamoyl, $C_{1-6}$ N-alkylcarbamoyl, $C_{1-6}$ N,N-dialkylcarbamoyl, nitro and cyano;

$R^{10}$ is hydrogen or $C_{1-10}$ alkyl;

$R^{11}$ $R^{11a}$, $R^{12}$ and $R^{12a}$ are (i) independently hydrogen or $C_{1-10}$ alkyl, or (ii) $R^{11}$ and $R^{12}$ taken together along with the nitrogen atom to which they are attached form a pyrrolidinyl, piperidinyl, azepinyl, or morpholine ring;

$R^{13}$ taken alone is selected from the group consisting of the side chain of a naturally occurring amino acids, optionally substituted phenyl and $C_{1-5}$ unbranched or branched alkyl;

$R^{14}$ taken alone is hydrogen, or $C_{1-6}$ alkyl; or, $R^{13}$ and $R^{14}$ taken together are $(CH_2)_3$;

X is a bond, O, S, NH;

n is 1 to 3;

o is 1 to 6; or, acid or base addition salts thereof.

DETAILED DESCRIPTION OF THE INVENTION

Unsubstituted pyridazinones of the present invention have very limited solubility which limits the ability to incorporate the compounds into formulations. While not wishing to be bound by any structural theory, substitution of the amide N—H with a bulky substituent weakens crystal packing forces and increases the solubility. Surprisingly the modified pyridazinones are efficiently absorbed through the GI tract and efficiently revert back to the unsubstituted amide moiety.

In an embodiment of the present invention there is provided a compound according to formula I wherein $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{12a}$, $R^{13}$, $R^{14}$, X, n and o are as defined hereinabove In another embodiment of the present invention there is provided a compound according to formula I wherein $R^3$ is hydrogen or fluoro; $R^4$ is selected from the group consisting of hydrogen, chloro, fluoro and methyl; $R^5$ is optionally substituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are independently selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, $R^1$, $R^2$, $R^9$, $R^{10}$, $R^{11a}$, $R^{12a}$, $R^{13}$, $R^{14}$, X, n and o are as defined hereinabove.

In another embodiment of the present invention there is provided a compound according to formula I wherein $R^1$ is methyl, ethyl, trifluoromethyl or halogen; $R^3$ is hydrogen or fluoro; $R^4$ is selected from the group consisting of hydrogen, chloro, fluoro and methyl; $R^5$ is optionally substituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are independently selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, $R^2$, $R^9$, $R^{10}$, $R^{11a}$, $R^{12a}$, $R^{13}$, $R^{14}$, X, n and o are as defined hereinabove.

In another embodiment of the present invention there is provided a compound according to formula I wherein $R^1$ is methyl, ethyl, trifluoromethyl or halogen; $R^3$ is hydrogen or fluoro; $R^4$ is selected from the group consisting of hydrogen, chloro, fluoro and methyl; $R^5$ is monosubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, $R^2$, $R^9$, $R^{10}$, $R^{11a}$, $R^{12a}$, $R^{13}$, $R^{14}$, X, n and o are as defined hereinabove.

In another embodiment of the present invention there is provided a compound according to formula I wherein $R^1$ is methyl, ethyl, trifluoromethyl or halogen; $R^3$ is hydrogen or fluoro; $R^4$ is selected from the group consisting of hydrogen, chloro, fluoro and methyl; $R^5$ is 2,5-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are selected from the consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, $R^2$, $R^9$, $R^{10}$, $R^{11a}$, $R^{12a}$, $R^{13}$, $R^{14}$, X, n and o are as defined hereinabove.

In another embodiment of the present invention there is provided a compound according to formula I wherein $R^1$ is methyl, ethyl, trifluoromethyl or halogen; $R^3$ is hydrogen or fluoro; $R^4$ is selected from the group consisting of hydrogen, chloro, fluoro and methyl; $R^5$ is 3,5-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, $R^2$, $R^9$, $R^{10}$, $R^{11a}$, $R^{12a}$, $R^{13}$, $R^{14}$, X, n and o are as defined hereinabove.

In another embodiment of the present invention there is provided a compound according to formula I wherein $R^1$ is methyl, ethyl, trifluoromethyl or halogen; $R^3$ is hydrogen or fluoro; $R^4$ is selected from the group consisting of hydrogen, chloro, fluoro and methyl; $R^5$ is 2,4-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, $R^2$, $R^9$, $R^{10}$, $R^{11a}$, $R^{12a}$, $R^{13}$, $R^{14}$, X, n and o are as defined hereinabove.

In another embodiment of the present invention there is provided a compound according to formula I wherein $R^1$ is methyl, ethyl, trifluoromethyl or halogen; $R^3$ is hydrogen or fluoro; $R^4$ is selected from the group consisting of hydrogen, chloro, fluoro and methyl; $R^5$ is 2,6-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, $R^2$, $R^9$, $R^{10}$, $R^{11a}$, $R^{12a}$, $R^{13}$, $R^{14}$, X, n, o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is optionally substituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O— and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is monosubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is phenyl substituted with halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio or $C_{1-6}$ haloalkoxy; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is methyl, ethyl or halogen; $R^2$ is hydrogen, halogen, methyl or ethyl; $R^3$ and $R^7$ are hydrogen; $R^4$ is selected from the group consisting of hydrogen, chloro, fluoro and methyl; $R^5$ is phenyl substituted with halogen, cyano, $C_{1-6}$ alkyl or $C_{1-6}$ haloalkyl; $R^6$ is $CH_2OH$, $CH_2OC(=O)XR^9$, $CH_2OCOCH(R^{13})NHR^{14}$ or $CH_2OP(=O)(OH)_2$; $R^8$ is selected from the group consisting of hydrogen, methyl and ethyl; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or —O—; and, $R^9$, $R^{10}$, $R^{11}$, $R^{12}$, $R^{13}$, $R^{14}$, n and o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^1$ is 2,5-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 2,5-disubstituted phenyl wherein each substituent is independently halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio or $C_{1-6}$ haloalkoxy; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl, $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is methyl, ethyl or halogen; $R^2$ is hydrogen, halogen, methyl or ethyl; $R^3$ and $R^7$ are hydrogen; $R^4$ is hydrogen, chloro, fluoro or methyl; $R^5$ is 2,5-disubstituted phenyl wherein each substituent is independently halogen, cyano, $C_{1-6}$ alkyl, $C_{1-6}$ haloalkyl; $R^6$ is $CH_2OH$, $CH_2OC(=O)XR^9$, $CH_2OCOCH(R^{13})NHR^{14}$ or $CH_2OP(=O)(OH)_2$; $R^8$ is selected from the group consisting of hydrogen, methyl and ethyl; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or O; and, $R^9$, $R^{10}$, $R^{13}$, $R^{14}$, n, o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 3,5-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 3,5-disubstituted phenyl wherein each substituent is independently halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio or $C_{1-6}$ haloalkoxy; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is halogen, methyl or ethyl; $R^2$ is hydrogen, halogen, methyl or ethyl; $R^3$ and $R^7$ are hydrogen; $R^4$ is hydrogen, chloro, fluoro or methyl; $R^5$ is 3,5-disubstituted phenyl wherein each substituent is independently halogen, cyano, $C_{1-6}$ alkyl, $C_{1-6}$ haloalkyl; $R^6$ is $CH_2OH$, $CH_2OC(=O)XR^9$, $CH_2OCOCH(R^{13})NHR^{14}$ or $CH_2OP(=O)(OH)_2$; $R^8$ is selected from the group consisting of hydrogen, methyl and ethyl; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or O; and, $R^9$, $R^{10}$, $R^{13}$, $R^{14}$, n and o are as defined hereinabove.

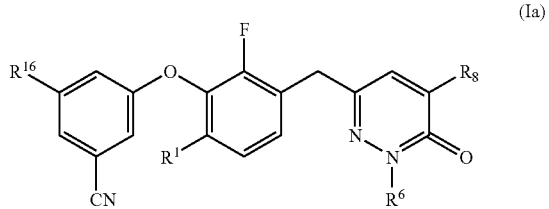

(Ia)

In another embodiment of the present invention there is provided a compound according to formula Ia wherein $R^1$ is fluoro, chloro, bromo or methyl; $R^6$ is $CH_2OH$, $CH_2OC(=O)XR^9$, $CH_2OCOCH(R^{13})NHR^{14}$ or $CH_2OP(=O)(OH)_2$; $R^8$ is hydrogen, methyl or ethyl; and, $R^{16}$ is $C_{1-6}$alkyl, $C_{3-8}$ cycloalkyl, $C_{1-6}$ haloalkyl, halogen or cyano; X is a bond or —O—; and, $R^9$, $R^{13}$ and $R^{14}$ are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 2,4-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 2,4-disubstituted phenyl wherein each substituent is independently halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio or $C_{1-6}$ haloalkoxy; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove.

In another embodiment of the present invention there is provided a compound according to formula I wherein $R^1$ is halogen, methyl or ethyl; $R^2$ is hydrogen, halogen, methyl or ethyl; $R^3$ and $R^7$ are hydrogen; $R^4$ is hydrogen, chloro, fluoro or methyl; $R^5$ is 2,4-disubstituted phenyl wherein each substituent is independently halogen, cyano, $C_{1-6}$ alkyl, $C_{1-6}$ haloalkyl; $R^6$ is $CH_2OH$, $CH_2OC(=O)XR^9$, $CH^2OCOCH(R^{13})NHR^{14}$ or $CH_2OP(=O)(OH)_2$; $R^8$ is selected from the group consisting of hydrogen, methyl and ethyl; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or O; and, $R^9$, $R^{10}$, $R^{13}$, $R^{14}$, n and o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 2,6-disubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 2,6-disubstituted phenyl wherein each substituent is independently halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio or $C_{1-6}$ haloalkoxy; $R^6$ is $CH_2OH$ $CH_2OC(=O)XR^9$, $CH_2OCOCH(R^{13})NHR^{14}$ or $CH_2OP(=O)(OH)_2$; $R^7$ hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove In another embodiment of the present invention there is provided a compound according to formula I wherein $R^1$ is halogen, methyl or ethyl; $R^2$ is hydrogen, halogen, methyl or ethyl; $R^3$ and $R^7$ are hydrogen; $R^4$ is hydrogen, chloro, fluoro or methyl; $R^5$ is 2,6-disubstituted phenyl wherein each substituent is independently halogen, cyano, $C_{1-6}$ alkyl, $C_{1-6}$ haloalkyl; $R^6$ is $CH_2OH$, $CH_2OC(=O)XR^9$, $CH^2COCH(R^{13})NHR^{14}$ or $CH_2OP(=O)(OH)_2$; $R^8$ is selected from the group consisting of hydrogen, methyl and ethyl; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or O; and, $R^9$, $R^{10}$, $R^{13}$, $R^{14}$, n, o are as defined hereinabove.

In another embodiment of the present invention there is provided a compound according to formula I wherein $R^1$ is methyl, ethyl, trifluoromethyl or halogen; $R^2$ is hydrogen, halogen, methyl or ethyl; $R^3$ is hydrogen or fluoro; $R^4$ is selected from the group consisting of hydrogen, chloro, fluoro and methyl; $R^5$ is 2,3,5-trisubstituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; $R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; X is a bond or —O—; and, $R^9$, $R^{10}$, $R^{11a}$, $R^{12a}$, $R^{13}$, $R^{14}$, n and o are as defined hereinabove In another embodiment of the present invention there is provided a compound according to formula I wherein $R^3$ and $R^4$ is selected from the group consisting of hydrogen, chloro, fluoro and methyl; $R^5$ is optionally substituted pyridinyl, pyridine N-oxide, indole, indole N-oxide, quinoline, quinoline N-oxide, pyrimidinyl, pyrazinyl or pyrrolyl; $R^6$ is $CH_2OH$, $CH_2OC(=O)XR^9$, $CH_2OCOCH(R^{13})NHR^{14}$ or $CH_2OP(=O)(OH)_2$; $R^7$ and $R^8$ are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio, halogen; X is a bond or O; and, $R^1$, $R^2$, $R^9$, $R^{10}$, $R^{11a}$, $R^{12a}$, $R^{13}$, $R^{14}$, n and o are as defined hereinabove.

In another embodiment of the present invention there is provided a compound according to formula I wherein the compound is:

Succinic acid mono-{3-[4-chloro-3-(3,5-dicyano-phenoxy)-2-fluoro-benzyl]-5-methyl-6-oxo-6H-pyridazin-1-ylmethyl}ester, Succinic acid mono-{3-[4-chloro-3-(3-chloro-5-cyano-phenoxy)-2-fluoro-benzyl]-5-methyl-6-oxo-6H-pyridazin-1-ylmethyl}ester, Succinic acid mono-{3-[4-bromo-3-(3,5-dicyano-phenoxy)-2-fluoro-benzyl]-5-methyl-6-oxo-6-H-pyridazin-1-ylmethyl}ester, Succinic acid mono-{3-[4-bromo-3-(3-chloro-5-cyano-phenoxy)-2-fluoro-benzyl]-5-methyl-6-oxo-6H-pyridazin-1-ylmethyl}ester, Succinic acid mono-{3-[4-chloro-3-(3-cyano-5-difluoromethyl-phenoxy)-2-fluoro-benzyl]-5-methyl-6-oxo-6H-pyridazin-1-ylmethyl}ester, Succinic acid mono-{3-[4-chloro-3-(3-cyano-5-fluoro-phenoxy)-2-fluoro-benzyl]-6-oxo-6H-pyridazin-1-ylmethyl}ester, Succinic acid mono-{3-[3-(3,5-dicyano-phenoxy)4-ethyl-2-fluoro-benzyl]-5-methyl-6-oxo-6H-pyridazin-1-ylmethyl}ester, Succinic acid mono-{3-[3-(3-chloro-5-cyano-phenoxy)4-ethyl-2-fluoro-benzyl]-5-methyl-6-oxo-6H-pyridazin-1-ylmethyl}ester, Succinic acid mono-{3-[3-(3-chloro-5-cyano-phenoxy)-2-fluoro-4-methyl-benzyl]-5-methyl-6-oxo-6H-pyridazin-1-ylmethyl}ester, Succinic acid mono-{3-[3-(3,5-dicyano-phenoxy)-2-fluoro-4-methyl-benzyl]-5-methyl-6-oxo-6H-pyridazin-1-ylmethyl}ester, or, Succinic acid mono-{3-[4-chloro-3-(3-cyano-5-difluoromethyl-phenoxy)-2-fluoro-benzyl]-6-oxo-6H-pyridazin-1-ylmethyl}ester.

In another embodiment of the present invention there is provided a method for treating an HIV-1 infection comprising administering to a host in need thereof a therapeutically effective amount of a compound of formula I wherein $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{12a}$, $R^{13}$, $R^{14}$, X, n, o are as defined hereinabove.

In another embodiment of the present invention there is provided a method for treating an HIV-1 infection comprising administering to a host in need thereof a therapeutically effective amount of a compound of formula I wherein $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{12a}$, $R^{13}$, $R^{14}$, X, n, o are as defined hereinabove.

In another embodiment of the present invention there is provided a method for treating an HIV-1 infection comprising administering to a host in need thereof a therapeutically effective amount of a compound of formula I wherein $R^1$ is methyl, ethyl, trifluoromethyl or halogen; $R^2$ and $R^4$ are independently hydrogen, fluoro, chloro, methyl or ethyl; $R^3$ is hydrogen or fluoro; $R^5$ is optionally substituted phenyl; $R^6$ is $CH_2OH$, $CH_2OC(=O)XR^9$, $CH_2OCOCH(R^{13})NHR^{14}$ or $CH_2OP(=O)(OH)_2$; $R^7$ is hydrogen, methyl or ethyl; and, X is a bond or —O—; and, $R^8$, $R^9$, $R^{10}$, $R^{11}$, $R^{12}$, $R^{13}$, $R^{14}$, n, o are as defined hereinabove.

In another embodiment of the present invention there is provided a method for treating an HIV-1 infection comprising administering to a host in need thereof a therapeutically effective amount of a compound of formula Ia wherein $R^1$ is fluoro, chloro, bromo or methyl; $R^6$ is $CH_2OH$, $CH_2OC(=O)XR^9$, $CH_2OCOCH(R^{13})NHR^{14}$ or $CH_2OP(=O)(OH)_2$; $R^8$ is hydrogen, methyl or ethyl; $R^{16}$ is selected from the group consisting of $C_{1-6}$ alkyl, $C_{3-8}$ cycloalkyl, $C_{1-6}$ haloalkyl, halogen and cyano; and, X is a bond or —O—; and, $R^{13}$, $R^{14}$, are as defined hereinabove.

In another embodiment of the present invention there is provided a method for inhibiting an HIV-1 reverse transcriptase comprising administering to a host in need thereof a therapeutically effective amount of a compound of formula I wherein $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{12a}$, $R^{13}$, $R^{14}$, X, n, o are as defined hereinabove.

In another embodiment of the present invention there is provided a method for inhibiting an HIV-1 reverse transcriptase wherein said reverse transcriptase exhibits at least one mutation compared to wild type virus comprising administering to a host in need thereof a therapeutically effective amount of a compound of formula I wherein $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{12a}$, $R^{13}$, $R^{14}$, X, n, o are as defined hereinabove.

In another embodiment of the present invention there is provided a method for treating an HIV-1 infection caused by a strain of HIV exhibiting reduced susceptibility to efavirenz, nevirapine or delavirdine comprising administering to a host in need thereof a therapeutically effective amount of a compound of formula I wherein $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{12a}$, $R^{13}$, $R^{14}$, X, n, o are as defined hereinabove.

In another embodiment of the present invention there is provided a composition comprising a therapeutically effective quantity of a compound of according to claim 1 in admixture with at least one pharmaceutically acceptable carrier, excipient or diluent sufficient upon administration in a single or multiple dose regimen for treating diseases mediated by human immunodeficieny virus.

In another embodiment of the present invention there is provided a process for preparing a compound of formula I wherein $R^6$ is $CH_2OH$, $CH_2OC(=O)XR^9$, $CH_2OCOCH(R^{13})NHR^{14}$; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or O and $R^1$, $R^2$, $R^3$, $R^4$, $R^5$, $R^7$ and $R^8$ are as defined in hereinabove, comprising the steps of:

(i) contacting a compound of formula I with formaldehyde or a formaldehyde equivalent, to produce a hydroxymethyl compound of formula I wherein $R^6$ is $CH_2OH$; optionally, (ii) contacting the resulting hydroxymethyl compound with an activated carboxylic acid derivative, Y—C(=O)XR$^9$ or Y—C(=O)CH(R$^{13}$)NR$^{14}$R$^{15}$ wherein R$^9$, R$^{13}$, R$^{14}$ are as defined hereinabove, or a heteroatom protected derivative thereof, R$^{15}$ is a nitrogen protecting group, and Y is a carboxylic acid activating group; and optionally, (iv) removing any protecting groups to afford a compound of formula I wherein $R^6$ is $CH_2OH$, $CH_2OC(=O)XR^9$, $CH_2OCOCH(R^{13})NHR^{14}$.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term "arylcarbonyl" as used herein means a group of formula C(=O)R wherein R is an aryl group; the term "benzoyl" as used herein an "arylcarbonyl" group wherein R is phenyl.

The term "acylamino" as used herein denotes a group of formula —NHC(=O)R wherein R is hydrogen or lower alkyl as defined herein.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. There may be optionally inserted along the alkyl group one or more oxygen, sulfur, substituted or unsubstituted nitrogen atoms. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents (preferably one substituent) selected from the other, specifically-named group. Thus, for example, "phenylalkyl" refers to an alkyl group having one to two phenyl substituents, and thus includes benzyl, phenylethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl)-3-hydroxypropyl, and so forth. Accordingly, as used herein, the term "hydroxyalkyl" is used to define a subset of heteroalkyl groups defined below. The term "(het)aryl" or "(hetero)aryl" is intended to refer to a situation in which the substituent is either an aryl ring or a heteroaryl ring as defined herein. The term (ar)alkyl is intened to refer to a situation in which the substituents is either an alkyl moiety or an aralkyl moiety as defined herein.

The terms "alkylsulfinyl" and "arylsulfinyl" as used herein denotes a group of formula —S(=O)R wherein R is alkyl or aryl respectively and alkyl and aryl are as defined herein.

The terms "alkylsulfonyl" and "arylsulfonyl" as used herein denotes a group of formula —S(=O)$_2$R wherein R is alkyl or aryl respectively and alkyl and aryl are as defined herein.

The term "alkylthio" or "thioalkyl" means an —S-alkyl group, wherein alkyl is as defined above. Examples of alkylthio groups include methylthio, ethylthio, n-propylthio, i-propylthio, n-butylthio, hexylthio, including their isomers. "Lower alkylthio" or "lower thioalkyl" as used herein denotes an alkylthio group with a "lower alkyl" group as previously defined. "$C_{1-10}$ alkylthio" as used herein refers to an —S-alkyl wherein alkyl is $C_{1-10}$.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)n-, RHN(CH$_2$)n-, and R$_2$N(CH$_2$)n-respectively wherein n is 1 to 6 and R is alkyl as defined above. "$C_{1-10}$ alkylamino" as used herein refers to an-aminoalkyl wherein alkyl is $C_{1-10}$.

The term "naturally occurring amino acids" as used herein means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Unless specifically indicated, all amino acids referred to in this application are in the L-form. The side chains of naturally occurring amino acids include: hydrogen, methyl, iso-propyl, iso-butyl, sec-butyl, —CH$_2$OH, —CH(OH)CH$_3$, —CH$_2$SH, —CH$_2$CH$_2$SMe, —(CH$_2$)$_p$COR wherein R is —OH or —NH$_2$ and p is 1 or 2, —(CH$_2$)$_q$—NH$_2$ where q is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene.

The term "aryl" as used herein denotes a monovalent aromatic carbocyclic radical containing 5 to 15 carbon atoms consisting of one individual ring, or one or more fused rings in which at least one ring is aromatic in nature, which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, indanyl, anthraquinolyl tetrahydronaphthyl, 3,4-methylenedioxyphenyl, 1,2,3,4-tetrahydroquinolin-7-yl, 1,2,3,4-tetrahydroisoquinoline-7-yl, and the like. The point of attachment of bicyclic aryl substituents with a heteroatom in one of the rings is on the carbocyclic aromatic ring.

The term "aryloxy group" as used herein means an O-aryl group wherein aryl is as defined above. An aryloxy group can be unsubstituted or substituted with one or more suitable substituents. Preferably, the aryl ring of an aryloxy group is a monocyclic ring, wherein the ring comprises 6 carbon atoms, referred to herein as "(C$_6$) aryloxy". The term "optionally substituted aryloxy" means the aryl or group may be substituted with one to three groups selected from the group consisting of $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio halogen, amino, alkylamino, dialkylamino, aminoacyl, acyl, alkoxycarbonyl, carbamoyl, N-alkylcarbamoyl, N,N-dialkylcarbamoyl, nitro and cyano The term "carbamoyl" as used herein means the radical —CONH$_2$. The terms "N-alkylcabamoyl" and "N,N-dialylcarbamoyl" mean a the radical CONHR' or CONR'R" respectively wherein the R' and R" groups are independently alkyl as defined herein. The prefix N-arylcabamoyl' denotes the radical CONHR' wherein R' is a an aryl radical as defined herein The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "C$_{3-7}$ cycloalkyl" as used herein refers to a cycloalkyl composed of 3 to 7 carbons in the carbocyclic ring.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "haloalkoxy" as used herein refers to a group —OR where R is haloalkyl as defined herein. The term "haloalkylthio" as used herein refers to a group —SR where R is haloalkyl as defined herein.

The term "halogen" or "halo" as used herein means fluorine, chlorine, bromine, or iodine.

The term "heteroalkyl" as used herein means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, or alkylamino. Representative examples include, but are not limited to, 2-hydroxyethyl, 3-hydroxypropyl, 2-hydroxy-1-hydroxymethylethy 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino,dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamnino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom. Nitrogen containing heteroaryl compounds include the corresponding N-oxides, e.g., pyridine N-oxide, quinioline N-oxide and the like.

The term "heteroaryloxy group" as used herein means an O-heteroaryl group, wherein heteroaryl is as defined above. The heteroaryl ring of a heteroaryloxy group can be unsubstituted or substituted with one or more suitable substituents. Examples of heteroaryl groups include, but are not limited to, 2-pyridyloxy, 3-pyrrolyloxy, 3-pyrazolyloxy, 2-imidazolyloxy, 3-pyrazinyloxy, and 4-pyrimidyloxy The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename; didanosine (ddI) available under the VIDEX tradename.; zalcitabine (ddC) available under the HIVID tradename; stavudine (d4T) available under the ZERIT trademark.; lamivudine (3TC) available under the EPIVIR tradename; abacavir (1592U89) disclosed in WO96/30025 and available under the ZIAGEN trademark; adefovir dipivoxil [bis(POM)-PMEA] available under the PREVON tradename; lobucavir (BMS-180194), a nucleoside reverse transcriptase inhibitor disclosed in EP-0358154 and EP-0736533 and under development by Bristol-Myers Squibb; BCH-10652, a reverse transcriptase inhibitor (in the form of a racemic mixture of BCH-10618 and BCH-10619) under development by Biochem Pharma; emitricitabine [(−)-FTC] licensed from Emory University under U.S. Pat. No. 5,814,639 and under development by Triangle Pharmaceuticals; beta-L-FD4 (also called beta-L-D4C and named beta-L-2',3'-dideoxy-5-fluoro-cytidene) licensed by Yale University to Vion Pharmaceuticals; DAPD, the purine nucleoside, (−)-beta-D-2,6,-diamino-purine dioxolane disclosed in EP-0656778 and licensed to Triangle Pharmaceuticals; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc.

The termn "non-nucleoside reverse transcriptase inhibitors" ("NNRTI"s) as used herein means non-nucleoside compounds that inhibit the activity of HIV-1 reverse transcriptase.

Typical suitable NNRTIs include nevirapine (BI-RG-587) available under the VIRAMUNE tradename; delaviradine (BHAP, U-90152) available under the RESCRIPTOR tradename; efavirenz (DMP-266) a benzoxazin-2-one disclosed in WO94/03440 and available under the SUSTIVA tradename; PNU-142721, a fuiropyridine-thio-pyrimide; AG-1549 (formerly Shionogi #S-1153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxy-methyl)-5-(1-methylethyl)-6-(phenylmethyl)-(2, 4(1H,3H)-pyrimidinedione); and (+)-calanolide A (NSC-675451) and B, coumarin derivatives disclosed in U.S. Pat. No. 5,489,697

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN as well as nonpeptide protease inhibitors e.g., VIRACEPT.

Typical suitable PIs include saquinavir available in hard gel capsules under the INVIRASE tradename and as soft gel capsules under the FORTOVASE tradename; ritonavir (ABT-538) available under the NORVIR tradename; indinavir (MK-639) available under the CRXIVAN tradename; nelffiavir (AG-1343) available under the VIRACEPT; amprenavir (141W94), tradename AGENERASE, a nonpeptide protease inhibitor; lasinavir (BMS-234475; originally discovered by Novartis, Basel, Switzerland (CGP-61755); DMP-450, a cyclic urea discovered by Dupont; BMS-2322623, an azapeptide under development by Bristol-Myers Squibb, as a 2nd-generation HIV-1 PI; ABT-378; AG-1549 an orally active imidazole carbamate.

Other antiviral agents include hydroxyurea, ribavirin, IL-2, IL-12, pentafuside and Yissum Project No. 11607. Hydroyurea (Droxia), a ribonucleoside triphosphate reductase inhibitor, the enzyme involved in the activation of T-cells. Hydroxyurea was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename as a lyophilized powder for IV infusion or sc administration upon reconstitution and dilution with water; a dose of about 1 to about 20 million 1 U/day, sc is preferred; a dose of about 15 million 1 U/day, sc is more preferred. IL-12 is disclosed in WO96/25171 and is available as a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 and available under the FUZEON tradename; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred.

Yissum Project No. 11607, a synthetic protein based on the HIV-1 Vif protein. Ribavirin, 1-.beta.-D-ribofuranosyl-1H-1,2,4-triazole-3-carboxamide, is described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include: (a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4.sup.+ and HIV-1-RNA plasma levels should be monitored every 3-6 months. Should viral load plateau, a fourth drug, e.g., one PI or one NNRTI could be added.

Preparation and Compounds

Compounds of the present invention can be made by a variety of methods depicted in the illustrative synthetic reaction schemes and examples shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry* II, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), diethyl iso-propylamine (DEIPA), pyridine (pyr), di-iso-butylaluminumhydride, DIBAL-H, room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds of the present invention are prepared by contacting the pyridazinone compounds 5 with formaldehyde to afford a hydroxymethyl compound 6. While the adducts are depicted herein as N-hydroxymethyl adducts, the pyridazinone ring, like a simple amide to which it is analogous, is an ambident nucleophile and a reaction can take place at either the nitrogen atom or the oxygen atom. The product of theses ambident nucleophiles can be influenced by subtle factors and both the N-hydroxymethyl or O-hydroxymethyl compounds are contemplated to be within the scope of the invention. Acylation of 6 affords esters (7: Y=alkyl or (hetero)aryl), carbonate (7: Y=O-alkyl or —O(hetero)aryl) or carbamates (7: Y=NH-alkyl or NH-(hetero)aryl)

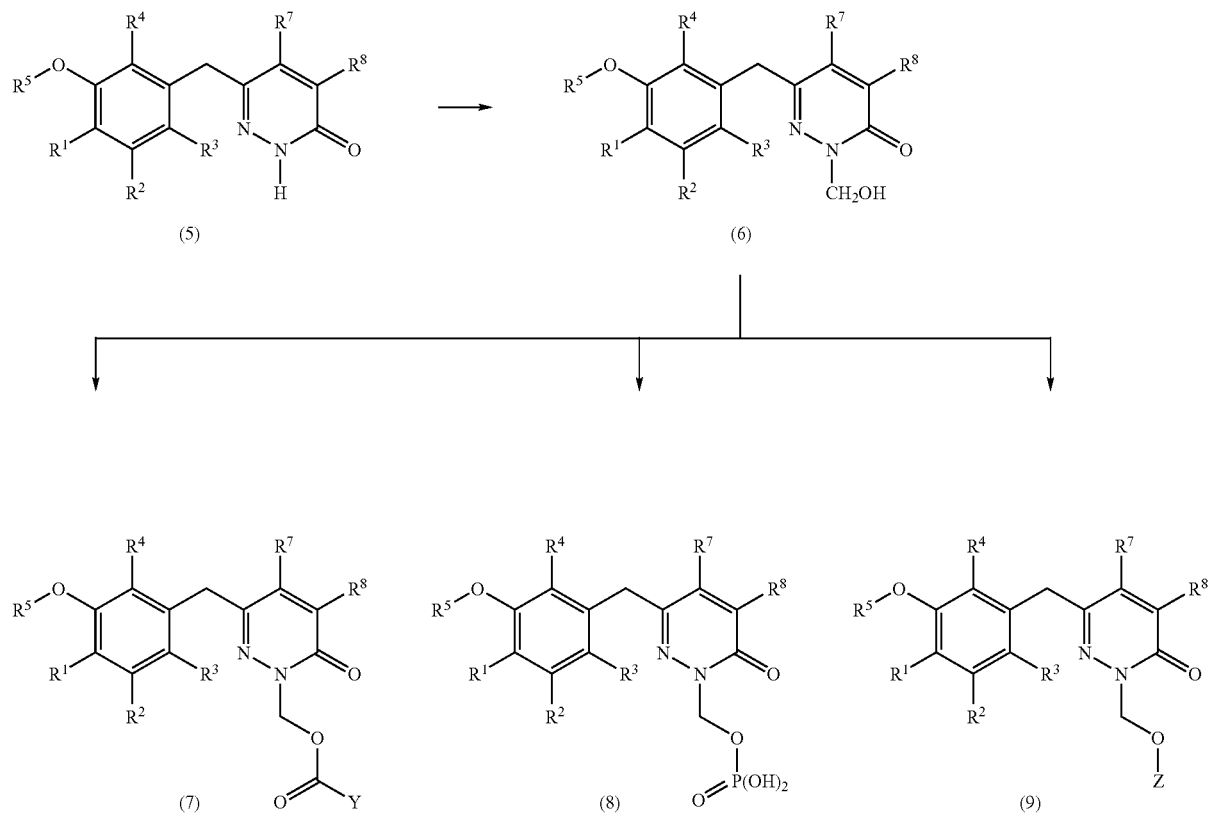

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, optionally in the presence of an inorganic or organic base (e.g., triethylamine or pyridine) at temperatures between −20 and 200° C., but preferably at temperatures between −10 and 80° C. The acylation may however also be carried out with the free acid in the presence of an acid-activating agent or a dehydrating agent, e.g. in the presence of isobutyl chloroformate, trimethylchlorosilane, N,N'-dicyclohexylcarbodiimide, N,N'-dicyclohexyl-carbodiimide/N-hydroxysuccinimide or 1-hydroxy-benzotriazole, N,N'-carbonyldiimidazole, O-(benzotriazol-1-yl)-N, N,N',N'-tetramethyl-uronium tetrafluoroborate/N-methylmorpholine, O-(benzotriazol-1-yl)-N,N,N',N'-tetramethyl-uronium tetrafluoroborate/DIPEA, N,N'-thionyldiimidazole or $(C_6H_5)_3P/CCl_4$, at temperatures between −20 and 200° C., but preferably at temperatures between −10 and 80° C. (J. March, *Advanced Organic Chemistry* John Wiley & Sons, New York 1992 392-398; J. Mulzer *Synthesis of Esters, Activated Esters & Lactones in Comprehensive Organic Synthesis*, E. Winterfeldt, ed., vol. 6, Pergamon Press, Oxford 1991, pp. 324-340)

Acylation of amino acids requires protection of the amino group must be protected prior to carrying out the esterification step. The various amino-protecting groups useful in this invention include N-benzyloxy-carbonyl-(cbz), tert-butoxy-carbonyl (Boc), N-formyl- and N-urethane-N-carboxy anhydrides which are all commercially available (SNPE Inc., Princeton, N.J., Aldrich Chemical Co., Milwaukee, Wis., and Sigma Chemical Co., St. Louis, Mo.) Protocols for efficient coupling of N-protected amino acids have been refined and extensively optimized (see e.g., M. Bodanszky, *Principles of peptide Synthesis*, Springer Verlag, New York 1993; P. Lloyd-Williams and F. Albericio *Chemical Methods for the Synthesis of peptides and Proteins* CRC Press, Boca Raton, Fla. 1997). Alternatively N carboxyanhydrides, cyclic amino acid anhydrides (William D. Fuller et al., *J. Am. Chem. Soc.* 1990 112:7414-7416 which is incorporated herein by reference in its entirety) can acylate the hydroxymethyl compound with concomitant liberation of the amino group.

Acylation with an alkoxychloroformate (e.g., ethoxychloroformate) or (hetero)aryloxy chloroformate affords carbonate compounds (7: Y=O-alkyl or —O(hetero)aryl). Carbonates are formally diesters of carbonic acid and are accessible from phosgene or its equivalents. Typically phosgene is introduced into a reaction mixture at low temperature containing an alcohol and base. N,N-dialkylamines or quaternary ammonium salts catalyze the reaction. The reaction can be stopped at the intermediate alkoxy chloroformate stage. The alkoxy chloroformate can then be used to make unsymmetrical carbonate esters. Condensation of alkoxychloroformates are carried out in a solvent such as methylene chloride, chloroform, carbon tetrachloride, ether, tetrahydrofuran, dioxane, benzene, toluene, acetonitrile, dimethylformamide, optionally in the presence of an inorganic or organic base (e.g., triethylamine or pyridine) at temperatures between −20 and 200° C., but preferably at temperatures between −10 and 80° C. Alternatives to the toxic gaseous phosgene include trichloromethylchloroformate (diphosgene) and bis-(trichloromethyl)carbonate (triphosgene) (H. Eckert and A. Nestl, *Functions Containing a Carbonyl Group and at least one Chalcogen (but no Halogen) in Comprehensive Organic Functional Group Transformations*, B. Trost (ed) Vol 6, E. Winterfeldt (volume editor) Pergamon Press Oxford, UK, 1995, pp 460-462; J. March, *Advanced Organic Chemistry*, John Wiley & Sons, NY, 1992 p. 392) Acylation with alkylaminocarbonyl chloride, (hetero)arylaminocarbonyl chloride, or with the correspond isocyanates, affords carbamate compounds (7: Y=NH-alkyl or —NH(hetero)aryl) (H. Eckert and A. Nestl, supra pp. 484-485)

Phosphates are prepared by contacting alcohols, phenols, primary and secondary amines, thiols phosphates and the like with pentavalent phosphorus compounds with a suitable leaving group. Suitably activated pentavalent phosphorus compounds include halophosphates, phosphoric-arene-sulfonic acid anhydrides pyrophosphates, phosphoramidates, phosphorthioates and triphenylphosphonium salts of phosphoric acid esters. Y. Hayakawa, *Inorganic Acid Derivatives* in *Comprehensive Organic Synthesis*, B. Trost (ed), vol. 6, E. Winterfeldt (vol ed) Pergamon Press, Oxford, UK, 1995 pp 602-615). Phosphorylation of heteroatoms can also be accomplished with trivalent phosphorus reagents which are subsequently oxidized to pentavalent phosphates. Trivalent phosphorylation reagents are usually more reactive than the pentavalent phosphorus compounds. Trivalent phosphorus reagents include phosphorochlorodites (chloroalkoxyphosphines), phosphoroamidites (dialkylaminodialkoxyphosphines) and phosphorothioites (alkylthiodialkoxyphosphites) (Y. Hayakawa, supra, pp 616-618). Phosphoroamidites are activated by weak acids such as N-methylanilinium tetrafluorborate, 1H-tetrazole, 5-methyltetrazole and the like. Contacting the phosphoroamidite with a weak base and an alcohol results in the formation of a phosphite which is oxidized, typically with meta-chloroperbenzoic acid. Alkoxy moieties are selected to allow facile hydrolysis or hydrogenoloysis when the free phosphoric acid or an salt thereof is sought. Commonly used phosphoroamidites include diethylamidites, diisopropylamidites or morpholidites. In vivo cleavage of the phosphate can mediated by serum phosphatases or by general acid catalysis.

Alkylation of 6 affords O-alkyl compounds 9 (Z=(hetero-substituted)alkyl). Ethers are typically prepared by alkylation of alkali metal alkoxides with a compound $RZ^1$ wherein $Z^1$ is a leaving group such as halo, $C_{1-4}$ alkanesulphonyloxy, benzenesulphonyloxy or p-toluenesulphonyloxy (Williamson Ether Synthesis). Common metals include sodium and potassium but the reactions is not limited to these metals. The alkoxide can be conveniently prepared by treating the alcohol with sodium hydride, potassium hydride or with sodium or potassium metal. The reaction is typically carried out in a solvent such as acetonitrile, DMF (dimethylformamide), DMSO (dimethylsulphoxide), 1,4-dioxane, THF or toluene, optionally in the presence of a phase transfer catalyst (J. March, *Advanced Organic Chemistry*, John Wiley & Sons, NY, 1992, pp. 386-387; J. Larock, *Comprehensive Organic Transformations*, Verlag Chemie, NY, 1989 (1st edition), pp. 446-448.).

Examples of representative compounds encompassed by the present invention and within the scope of the invention are provided in Table I. These examples and preparations which follow are provided to enable those skilled in the art to more clearly understand and to practice the present invention. They should not be considered as limiting the scope of the invention, but merely as being illustrative and representative thereof.

TABLE I

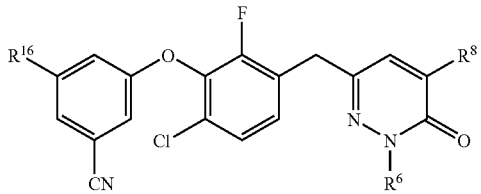

| No. | R⁶ | R¹⁶ | R⁸ | Mol. wt (MS) | MP | $C_{max}$ μg/mL | AUC μg h/mL |
|---|---|---|---|---|---|---|---|
| I-1 | CH₂OH | CN | Me | 424.82 (425) | 172-179 | 2.3 | 31 |
| I-2 | 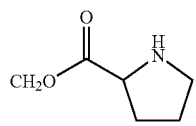 | CN | Me | 521.93 (522) | 163.0-164.8 | 3 | 43 |
| I-3 | CH₂OC(=O)CH₂NH₂ | CN | Me | 481.87 (482) | 161.8-162.6 | 2.5 | 37 |
| I-4 | CH₂OC(=O)CHMe₂ | CN | Me | 494.91 (494) | | ND | ND |
| I-5 | CH₂OC(=O)CH(NH₂)CHMe₂ (L)-isomer | CN | Me | 523.95 (524) | 176.7-178.3 | 3.6 | 53 |
| I-6 | CH₂OC(=O)Me | CN | Me | 466.85 (466) | 168.4-169.8 | ND | ND |
| I-7 | 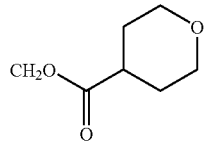 | CN | Me | 536.95 (537) | | ND | ND |
| I-8 | CH₂OC(=O)(CH₂)₂CO₂H | CN | Me | 524.89 (524) | 167-171.5 | 5.2 | 56 |
| I-9 | CH₂O(Z)C(=O)CH=CHCO₂H | CN | Me | 522.87 (523) | 120.5-125.4 | 4.8 | 65 |
| I-10 | CH₂OC(=O)CH(NH₂)CH(Et)Me | CN | Me | 539.99 (540) | 196.0-198.3 | 4.7 | 66 |
| I-11 | CH₂OC(=O)CH(NH₂)Ph | CN | Me | 559.98 (560) | 183.5-186.9 | 4.7 | 69 |
| I-12 | CH₂OCO₂CHMe₂ | CN | Me | 510.91 (511) | — | ND | ND |
| I-13 | CH₂OCO₂CH₂Ph | CN | Me | 558.95 (559) | — | ND | ND |
| I-14 | 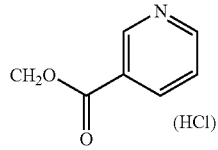 (HCl) | CN | Me | 529.91 (530) | 173.6-174.2 | 3.5 | 40 |
| I-15 | 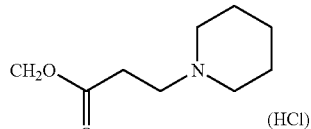 (HCl) | CN | Me | 564.01 (565) | 63.3-65.2 | 4.9 | 70 |
| I-16 | 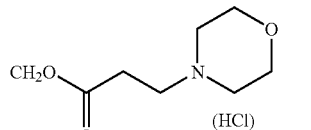 (HCl) | CN | Me | 565.99 (566) | 126.0-133 | 4.2 | 61 |

TABLE I-continued

[Structure: R16-substituted phenyl-O-(2-F, 4-Cl phenyl)-CH2-pyridazinone with R8 and N-R6 substituents; R16 phenyl bears CN]

| No. | R⁶ | R¹⁶ | R⁸ | Mol. wt (MS) | MP | $C_{max}$ μg/mL | AUC μg h/mL |
|---|---|---|---|---|---|---|---|
| I-17 | CH₂O-C(=O)-O-CH₂CH₂-N(morpholine) (HCl) | CN | Me | 581.98 (582) | 79-101 | 2.2 | 35 |
| I-18 | CH₂OCO₂(CH₂)₂NMe₂ | CN | Me | 539.95 (540) | 75-90 | 2.9 | 48 |
| I-19 | CH₂OC(=O)CH(NH₂)CH(CH₃)₂ (L)-isomer | Cl | Me | 534.39 | | | |
| I-20 | CH₂OC(=O)CH(NH₂)CH₂CONH₂ (L)-isomer | Cl | Me | 539.93 (540) | 147.0-150.2 | 2.9 | 35 |
| I-21 | CH₂OC(=O)(CH₂)₂CO₂H | Cl | Me | 534.32 | | | |
| I-22 | CH₂OH | Cl | Me | 434.25 | | | |
| I-23 | CH₂O—P(=O)(—O⁻Na⁺)₂ | CN | Me | 504.8 (503) | 193.7-197.2 | | |
| I-24 | (CH₂)₂OC(=O)Ph | CN | Me | 542 (543) | 145.7-149.9 | ND | |
| I-25 | (CH₂)₂OH | CN | Me | 438 (439) | 128.5-132.9 | ND | |
| I-26 | CH₂CO₂H | CN | Me | 452 (452) | 194.3-197.7 | ND | |
| I-27 | CH₂OH | CHF₂ | Me | 451 (450) | 113.9-117.3 | ND | |
| I-28 | CH₂OC(=O)(CH₂)₂CO₂H | CHF₂ | Me | 551 (550) | 154.3-156.9 | 4.3 | 78.2 |
| I-29 | CH₂OH | F | H | 404 (403) | 100.5-103.8 | ND | |
| I-30 | CH₂OC(=O)(CH₂)₂CO₂H | F | H | 504 (503) | 133.9-137.0 | 12 | 240 |
| I-31 | CH₂OC(=O)(CH₂)₂CO₂H | CHF₂ | H | 536 (535) | ND | 11.0 | 144 |

[Structure at bottom: NC-substituted phenyl-O-(2-F, 4-Cl phenyl)-CH2-pyridazinone with R substituent and Me]

| | | | $C_{max}$ | AUC |
|---|---|---|---|---|
| 10: R = CN | | | 0.6 | 8.1 |
| 11: R = Cl | | | 2.3 | 30.0 |
| dosed p.o. at 50 mg/kg | | | | |

¹$C_{max}$ represents the peak concentration of active nnRTI
²AUC represents total amount of active nnRTI absorbed.
³Prodrugs were administered orally at a dose equimolar to the parent compound administered at 150 mg/kg

Dosage and Administration

The compounds of the present invention may be formulated in a wide variety of oral administration dosage forms and carriers. Oral administration can be in the form of tablets, coated tablets, dragees, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. Anti-HIV therapy usually includes multiple anti-HIV drugs and pharmaceutical compositions of the present invention may contain one or more other anti-HIV drugs in addition to compounds of the present invention. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing infections. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLE 1

5-[6-Chloro-2-fluoro-3-(1-hydroxymethyl-5-methyl-6-oxo-1,6-dihydro-pyridazin-3-ylmethyl)-phenoxyl]-isophthalonitrile

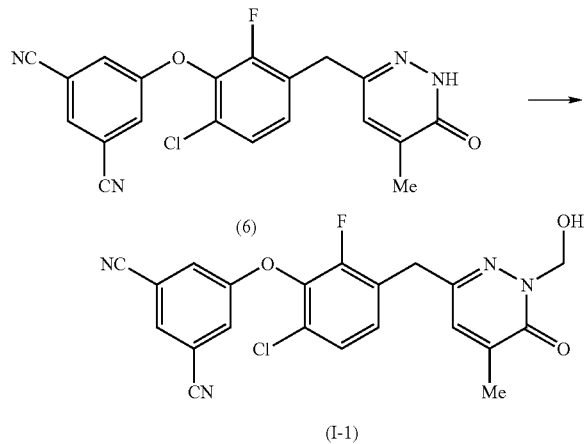

A suspension of pyridazinone 6 (3.3 g, 8.4 mmol) in MeOH (55 mL) and 37% aqueous formaldehyde (15 mL, 185 mmol) was heated to reflux for 2.5 h and then allowed to stand at ambient temperature for 1 h. The mixture was diluted with 20 mL of water and filtered. The resulting white solid was dried at 50° C. for 16 h in vacuo to afford I-1 as a white solid (3.3 g, 7.7 mmol): mp 172-179° C.; $^1$H NMR (d$_6$-DMSO, 300 MHz) δ 8.22 (t, J=1.2 Hz, 1H), 7.93 (d, J=1.2 Hz, 2 H), 7.50 (dd, J=1.5, 8.4 Hz, 1 H), 7.35 (t, J=7.5 Hz, 1 H), 7.25 (apparent d, J=1.2 Hz, 1H), 6.60 (t, J=7.5 Hz, 1 H), 5.27 (d, J=7.5 Hz, 2 H), 3.98 (s, 2 H), 2.06 (d, J=1.2 Hz, 3 H); $^{13}$C NMR (75 MHz) δ 160.3, 157.3, 154 (d), 144.4, 140.7, 137.3 (d), 131.4, 130.7, 129.5, 127.0 (d), 126.4, 123.7, 116.8, 114.8, 73.8, 33.5, 16.5; ESMS m/z 425 (M)$^+$; Anal. Calcd. for $C_{21}H_{14}FClN_4O_3$: C, 59.37; H, 3.32; N, 13.19. Found: C, 59.08; H, 3.18; N, 13.14.

Compounds I-22, I-27 and I-29 can be prepared in similar manner except 5-[6-chloro-2-fluoro-3-(5-methyl-6-oxo-1,6-dihydro-pyridazin-3-ylmethyl)-phenoxy]-isophthalonitrile was replaced with 3-chloro-5-[6-chloro-2-fluoro-3-(5-methyl-6-oxo-1,6-dihydro-pyridazin-3-ylmethyl)-phenoxy]-benzonitrile, 3-[6-chloro-2-fluoro-3-(5-methyl-6-oxo-1,6-dihydro-pyridazin-3-ylmethyl)-phenoxy]-5-difluoromethyl-benzonitrile and 3-[6-chloro-2-fluoro-3-(5-methyl-6-oxo-1,6-dihydro-pyridazin-3-ylmethyl)-phenoxy]-5-difluoromethyl-benzonitrile respectively.

EXAMPLE 2

(S)-1-{3-[4-Chloro-3-(3,5-dicyano-phenoxy)-2-fluoro-benzyl]-5-methyl-6-oxo-6H-pyridazin-1-yl-methoxycarbonyl}-2-methyl-propyl-ammonium; chloride

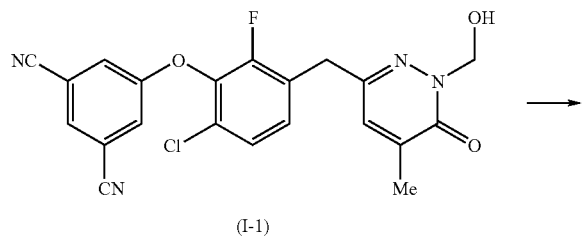

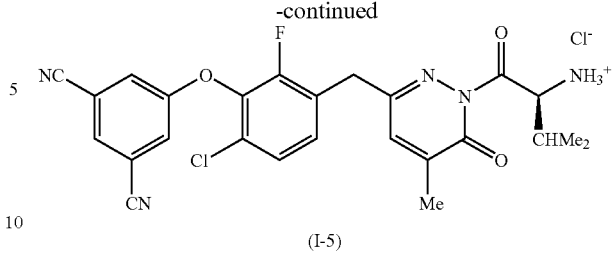

A DMF (25 mL) solution of I-1 (4.5 g, 10.6 mmol) was generated at ambient temperature and without delay treated with TEA (0.3 mL, 2.1 inmol) and a toluene (15 mL) solution N-tert-butoxycarbonyl (S)-valine N-carboxyanhydride (3.1 g, 12.7 mmol). The resulting solution was stirred for 2 h and poured into water (120 mL) and extracted with 2:1 hexane:EtOAc (4×100 mL). The combined organic extracts were with washed brine, dried over anhydrous sodium sulfate, and loaded onto a pad of silica gel and eluted with EtOAc. The desired N-Boc amino ester was obtained (5.6 g, 8.9 mmol) as a foam and was dissolved in ethyl acetate at ambient temperature and treated with hydrochloric acid (4 mL, 4 M solution in 1,4-dioxane). A white precipitate formed and stirring was continued for 14 h, ethyl ether (25 mL) was added and the suspension was stored at 0° C. The crude solid was collected and dissolved in warm iso-propanol and EtOAc and then stored at ambient temperature for 18 h. The amine hydrochloride I-5 (1.3 g, 2.3 mmol) was filtered and dried: mp 176.7-178.3° C.; Anal. Calcd for $C_{26}H_{23}FClN_5O_4HCl$: C, 55.72; H, 4.32; N, 12.50. Found: C, 55.71; H, 4.28; N, 12.35.

Compounds I-2, I-3, I-10 and I-11 can be prepared in similar manner to I-5 except N-tert-butoxycarbonyl (S)-valine N-carboxyanhydride was replaced by the N-carboxy-anhydrides of proline, glycine, isoleucine and phenylglycine respectively. Compound I-19 can be prepared in similar manner to I-5 except I-1 was replaced 3-chloro-5-[6-chloro-2-fluoro-3-(1-hydroxymethyl-5-methyl-6-oxo-1,6-dihydro-pyridazin-3-ylmethyl)-phenoxy]-benzonitrile (I-22). Compound I-20 can be prepared in similar manner to I-5 except I-1 was replaced with I-22 and N-tert-butoxycarbonyl (S)-valine N-carboxyanhydride was replaced with the N-carboxy anhydride of asparagine.

EXAMPLE 3

Succinic acid mono-{3-[4-chloro-3-(3,5-dicyano-phenoxy)-2-fluoro-benzyl]-5-methyl-6-oxo-6H-pyridazin-1-ylmethyl}ester

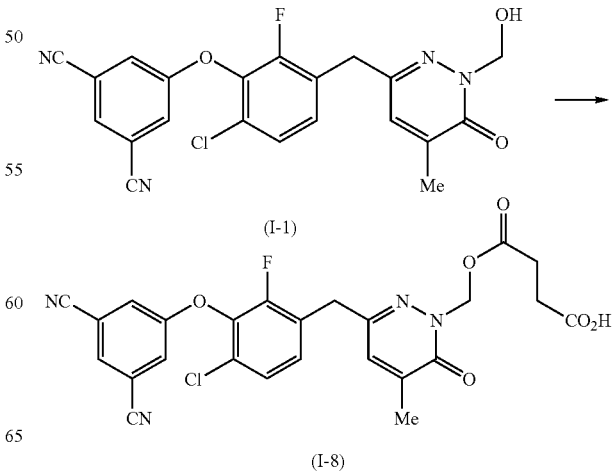

To an ice-cold solution of succinic acid (2.44 g, 20.6 mmol), triethylamine (3.6 mL, 26 mmol), 4-dimethylaminopyridine (127 mg, 1.05 mmol), isopropenylchloroformate (0.80 mL, 7.3 mmol) in dichloromethane (110 mL) was added a solution of I-1 (3.13 g, 5.2 mmol) and DCM (150 mL). The effervescing solution was stirred at 0° C. for 1.5 h and poured into 30 mL of 10% aqueous HOAc. The mixture was extracted with ethyl acetate (4×50 mL) and the combined extracts dried over sodium sulfate. The volatile solvents were evaporated and the residue was loaded onto a pad of flash silica gel and washed with 2:1 EtOAc:hexane. The desired product was eluted with 0.5% acetic acid in 3:1 EtOAc:hexane and recrystallized from warm ethyl acetate and hexane (1.1 g) to afford I-8 (1.36 g): mp 170.1-171.6° C.; $^1$H NMR (d$_6$-DMSO, 300 MHz) δ 12.2 (br.s, 1 H), 8.22 (t, J=1.2 Hz, 1 H), 7.95 (d, J=1.2 Hz, 2 H), 7.51 (dd, J=1.5, 8.4 Hz, 1 H), 7.35 (t, J=7.5 Hz, 1 H), 7.30 (apparent d, J=1.2 Hz, 1 H), 5.89 (s, 2 H), 3.99 (s, 2 H), 2.50 (t, J=1.5 Hz, 4 H), 2.07 (d, J=1.2 Hz, 3 H); $^{13}$C NMR (75 MHz) δ 171.9, 169.9, 158.7, 155.6, 152 (d), 144.0, 139.2, 135.6, 135.4, 129.75, 129.6, 127.8, 127.7, 124.9, 124.8, 124.7, 122.1, 115.1, 113.1, 71.6, 31.8, 14.7; ESMS m/z 525 (M$^{+1}$)$^+$; Anal. Calcd for C$_{25}$H$_{18}$FClN$_4$O$_6$: C, 57.20; H, 3.46; N, 10.68. Found: C, 57.26; H, 3.61; N, 10.52.

Compound I-9 was prepared in a similar manner to I-8 except succinc acid was replaced with maleic acid. Compounds I-4, I-6, I-7, I-14, I-15, I-16 were prepared in similar manner to I-8 except succinic acid was replaced with iso-butyric acid, acetic acid, tetrahydropyran-4-carboxylic acid, nicotinic acid, 3-piperidin-1-yl-propionic acid and 3-morpholin-4-yl-propionic acid respectively. The acylations can also be conveniently carried out with the corresponding carboxylic acid chloride. I-21, I-28, I-30 and I-31 were prepared in a similar manner to I-8 except 5-[6-chloro-2-fluoro-3-(5-methyl-6-oxo-1,6-dihydro-pyridazin-3-ylmethyl)-phenoxy]-isophthalonitrile was replaced with 3-chloro-5-[6-chloro-2-fluoro-3-(5-methyl-6-oxo-1,6-dihydro-pyridazin-3-ylmethyl)-phenoxy]-benzonitrile, 3-[6-chloro-2-fluoro-3-(5-methyl-6-oxo-1,6-dihydro-pyridazin-3-ylmethyl)-phenoxy]-5-difluoromethyl-benzonitrile, 3-[6-chloro-2-fluoro-3-(5-methyl-6-oxo-1,6-dihydro-pyridazin-3-ylmethyl)-phenoxy]-5-fluoro-benzonitrile and 3-[6-chloro-2-fluoro-3-(6-oxo-1,6-dihydro-pyridazin-3-ylmethyl)-phenoxy]-5-difluoromethyl-benzonitrile respectively

EXAMPLE 4

Carbonic acid 3-[4-chloro-3-(3,5-dicyano-phenoxy)-2-fluoro-benzyl]-5-methyl-6-oxo-6H-pyridazin-1-ylmethyl ester 2-dimethylamino-ethyl ester

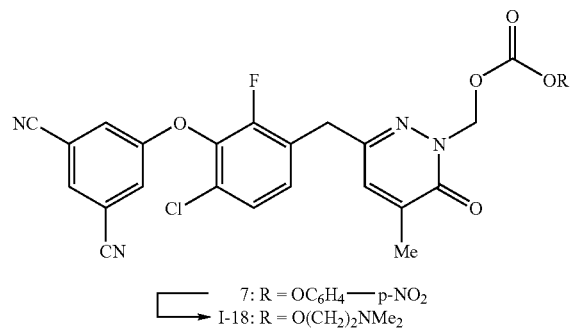

A DCM (10 mL) solution of hydroxymethyl pyridazinone I-1 (600 mg, 1.4 mmol) was cooled 0° C. and treated with TEA (0.6 mL, 4.2 mmol), DMAP (85 mg, 0.71 mmol), and p-nitrophenoxychloroformate (571 mg, 2.8 mmol). The yellow solution was stirred at 0° C. for 2 h and poured into 30 mL of aqueous sodium bicarbonate. The mixture was extracted with EtOAc (4×50 mL) and dried over sodium sulfate. After removal of the volatiles, the residue was loaded onto a pad of flash silica and the product (170 mg, 0.3 mmol) was eluted with 1:2 EtOAc:hexane to afford 7. The intermediate phenoxycarbonate 7 was dissolved in MeCN (12 mL) and DCM (10 mL) at ambient temperature and treated with 2-(N,N-dimethylamino)ethanol (0.1 mL, 1.1 mmol). After stirring for 16 h, the mixture was poured into aqueous sodium bicarbonate and extracted with EtOAc (3×25 mL) and dried over anhydrous sodium sulfate. The crude carbonate (85 mg) was dissolved in EtOAc and treated with hydrochloric acid (0.5 mL, 1 M Et$_2$O) and aged for 18 h at rt. The precipitated amine HCl salt I-18 was filtered and the volatiles were removed in vacuo.

I-17 was prepared in similar manner to I-18 except 2-(N,N-dimethylamino)ethanol was replaced with 4-(2-hydroxyethyl)morpholine. I-12 and I-13 were prepared in similar manner to I-18 except the two ste sequence utilizingp-nitrophenoxychloroformate and 2-(N,N-dimethylamino)ethanol was replaced by direct condensation with iso-propyl-chloroformate and benzyl-chloroformate respectively.

EXAMPLE 5

Phosphoric acid mono-{3-[4-chloro-3-(3,5-dicyanophenoxy)-2-fluoro-benzyl]-5-methyl-6-oxo-6H-pyridazin-1-ylmethyl}ester disodium salt

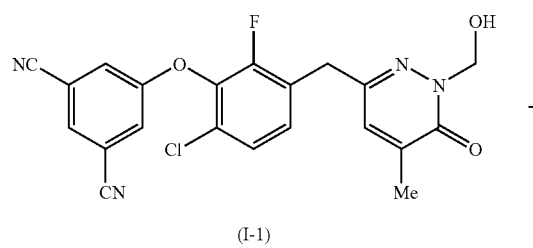

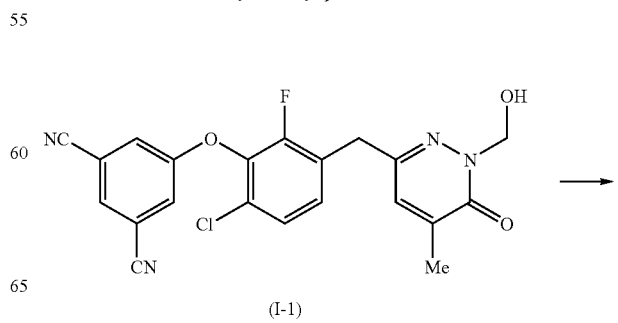

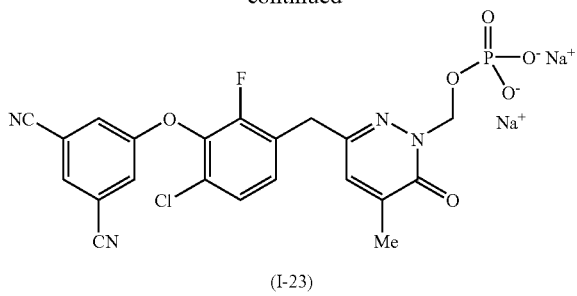

(I-23)

A 100 mL roundbottom flask was charged with 1-H tetrazole (225 mg, 3.2 mmol), I-1 (90% purity, 682 mg, 1.4 mmol) and acetonitrile (10 mL). To the solution was added dropwise over three minutes the bis-(2-cyanoethyl)-N,N-diisopropyl phosphoramidite (Spectrum Chemicals, 871 mg, 3.2 mmol). The mixture stirred for 16 h at rt, filtered and concentrated to yield 1.5 grams of a clear oil. The desired phosphite was purified by flash chromatography on silica gel (60-90% EtOAc/hexanes) to yield 866 mg (100%) as a clear oil which was immediately dissolved in DCM (14 mL). The solution was cooled to 0° C. and solid m-chloroperbenzoic acid (Aldrich Co. 77% purity, 326 mg, 1.45 mmol) was added. The reaction was stirred for 4 h at 0° C. and treated with 1 M $Na_2S_2O_4$ and extracted twice with dichloromethane. The organic layers were combined, dried over $MgSO_4$, filtered and concentrated. The crude product was purified by flash chromatography on silica gel (0-2% methanol/ethyl acetate) to yield 620 mg (69%) as a white foam. The phosphate triester (612 mg, 1.0 mmol) and suspended in MeCN (2.5 mL) and concentrated aqueous ammonia (10 mL) was added and the reaction mixture stirred for 48 h. Another portion of ammonia (5 mL) was added and stirring was continued for an additional 24 h. The suspension was then filtered and washed with acetonitrile to obtain 456 mg (86%) of the desired product as a white ammonium salt. A portion of this was run through a Dowex 50X2 ($Na^+$) to afford I-23 as an off-white sodium salt.

EXAMPLE 6

5-{6-Chloro-2-fluoro-3-[1-(2-hydroxy-ethyl)-5-methyl-6-oxo-1,6-dihydro-pyridazin-3-ylmethyl]-phenoxy}-isophthalonitrile

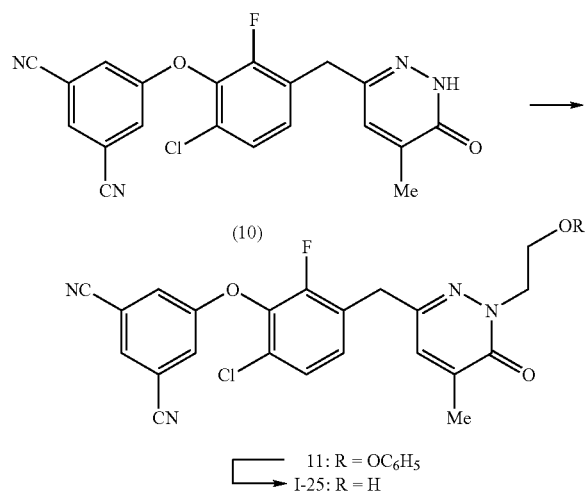

11: R = $OC_6H_5$
I-25: R = H

Pyridazinone 10 (890 mg, 2.2 mmol) and 2-bromoethyl benzoate (0.38 mL, 2.4 mmol) were dissolved in N,N-dimethylformamide (15 mL) and cooled to 0° C. under an argon atmosphere. Sodium hydride (95% Aldrich, 68 mg, 2.8 mmol) was added in one portion and the mixture was allowed to warm to ambient temperature. After 20 h, the desired benzoate ester was isolated by partitioning the reaction mixture between water and 1:1 hexane:EtOAc, drying over sodium sulfate, and filtration of the crude product through a pad of flash silica gel: mp 145.7-149.9° C.; ESMS m/z 543 $(M^{+1})^+$; Anal. Calcd. for $C_{29}H_{20}FClN_4O_4$: C, 64.15; H, 3.71; N, 10.32. Found: C, 63.77; H, 3.72; O, 10.01.

The γ-hydroxyethyl amine was obtained by dissolving the benzoate ester (640 mg, 1.1 mmol) in a solution of lithium hydroxide (105 mg, 2.5 mmol) in water (5 mL) and THF (30 mL) at ambient temperature. After 16 h at room temperature the volatile solvents were evaporated and the crude product I-25 was loaded onto a pad of silica and eluted with EtOAc: mp 128.5-132.1° C.; ms $[M+H]^+$=439.

EXAMPLE 7

{3-[4-Chloro-3-(3,5-dicyano-phenoxy)-2-fluoro-benzyl]-5-methyl-6-oxo-6H-pyridazin-1-yl}-acetic acid

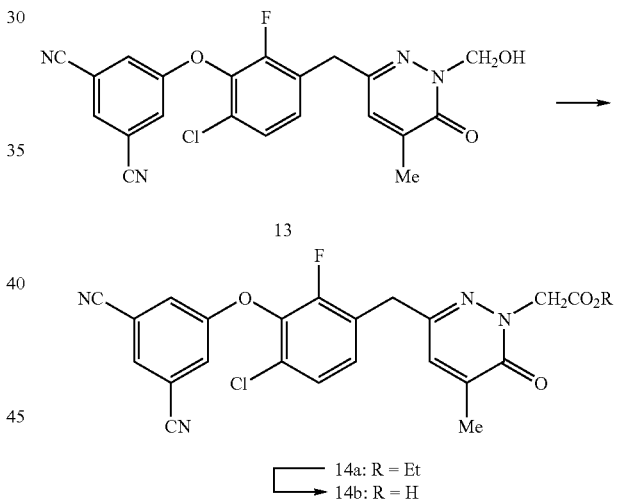

14a: R = Et
14b: R = H

Step 1

A flask was charged with 13 (0.830 g, 2.12 mmol), $Cs_2CO_3$ (0.760 g, 2.33 mmol), ethyl bromoacetate (0.25 mL, 2.24 mmol) and N-methylpyrrolidone (15 mL). The suspension was stirred vigorously at RT for 2 d. The reaction mixture was poured into water (80 mL) and twice extracted with EtOAc/hexane (2:1). The combined extracts were washed sequentially with brine, water and brine and then dried ($Na_2SO_4$). The solution was filtered and the filtrate concentrated in vacuo. The crude product was adsorbed onto a pad of $SiO_2$ and eluted with a 1:1 to 2:1 EtOAc/hexane gradient to afford 0.250 g of 14a as a white solid which was used directly in the next step.

Step 2

To a solution of 14a (0.250 g0 dissolved in THF (20 mL) was added a solution of $LiOH \cdot H_2O$ (0.050 g) and water (5 mL) and the resulting mixture stirred for 1.5 h at RT. The reaction mixture was diluted with sufficient toluene and water to produce a two-phase mixture. The aqueous phase was acidified with 1M HCl and twice extracted with EtOAc. The combined EtOAc extracts were dried (Na$_2$SO$_4$), filtered and concentrated in vacuo to afford a foam. The crude product was recrystallized from 4 mL of EtOAc/EtOH (1:1) to afford 14b: mp 194.3-197.7° C.

EXAMPLE 8 dose equivalent to (0.127 mmol) was administered orally by gavage. A blood sample (0.3 mL) was collected from the treated rats at 0.5, 1, 2, 3, 4, 6 and 8 hours after via the jugular cannula. A sample of at least 0.3 mL of blood was withdrawn from the untreated animals 3 h after dosing. After 24 h from dosing, as much blood as possible was collected from all treated and control animals. Potassium oxalate/NaF was added to the samples which were stored on ice during sampling procedure. The samples were spun in a refrigerated centrifuge at −4° C. as soon as possible and the plasma samples were stored −20° C. immediately after centrifugation amd later transferred to a −80° C. freezer until analysis. The concentration of test compound was determined by hplc.

EXAMPLE 9

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |

-continued

| Composition for Oral Administration (C) | |
|---|---|
| Ingredient | % wt./wt. |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I

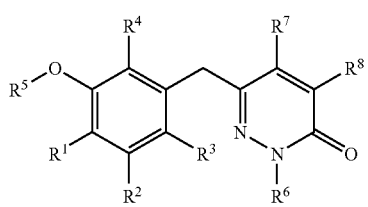

(I)

wherein;

$R^1$, $R^2$, $R^3$ and $R^4$ are each independently selected from the group consisting of hydrogen, $C_{1-6}$ alkyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ haloalkylthio, halogen, amino, alkylamino, dialkylamino, acylamino, nitro and cyano;

$R^5$ is aryl or heteroaryl radical said heteroaryl radical selected from the group consisting of pyridinyl, pyridine N-oxide, indole, indole N-oxide, quinoline, quinoline N-oxide, pyrimidinyl, pyrazinyl and pyrrolyl; wherein, said aryl and said heteroaryl radicals are optionally substituted with one to three substituents independently selected from the group consisting of $C_{1-6}$ alkyl, $C_{2-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ sulfonyl, $C_{1-6}$ haloalkoxy, $C_{1-6}$ haloalkylthio, hydroxy, halogen, amino, $C_{1-6}$ alkylamino, $C_{1-6}$ dialkylamino, acylamino, acyl, $C_{1-6}$ alkoxycarbonyl, carbamoyl, $C_{1-6}$ N-alkylcarbamoyl, $C_{1-6}$ N,N-dialkylcarbamoyl, nitro and cyano;

$R^6$ is selected from the group consisting of $CH_2OH$, $CH_2CH_2OH$, $CH_2OC(=O)XR^9$, $CH_2CH_2OC(=O)XR^9$, $CH_2OCOCH(R^{13})NHR^{14}$, $CH_2CO_2R^{10}$, $CH_2NR^{11}R^{12}$, $CH_2OP(=O)(OH)_2$ and $CH(NR^{11}R^{12})CO_2R^{10}$;

$R^7$ and $R^8$ taken independently are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with one or two substituents independently selected from the group consisting of hydroxy, alkoxy, thiol, alkylthio, $C_{1-6}$ alkylsulfinyl, $C_{1-6}$ alkylsulfonyl, halogen and N-morpholinyl;

$R^9$ is $C_{1-10}$ alkyl, $C_{1-10}$ heteroalkyl, $(CH_2)_oCO_2H$, $CH=CHCO_2H$, aryl, $(CH_2)_nNR^{11a}R^{12a}$ or heteroaryl said aryl and said heteroaryl optionally substituted with one to three substituents independently selected from the group consisting of $C_{1-6}$ alkyl, $C_{2-6}$ alkenyl, $C_{1-6}$ haloalkyl, $C_{3-8}$ cycloalkyl, $C_{1-6}$ alkoxy, $C_{1-6}$ alkylthio, $C_{1-6}$ alkylsulfinyl, $C_{1-6}$ alkyl sulfonyl, $C_{1-6}$ haloalkoxy, $C_{1-6}$ haloalkylthio, hydroxy, halogen, amino, $C_{1-6}$ alkylamino, $C_{1-6}$ dialkylamino, acylamino, acyl, $C_{1-6}$ alkoxycarbonyl, carbamoyl, $C_{1-6}$ N-alkylcarbamoyl, $C_{1-6}$ N,N-dialkylcarbamoyl, nitro and cyano;

$R^{10}$ is hydrogen or $C_{1-10}$ alkyl;

$R^{11}$ $R^{11a}$, $R^{12}$ and $R^{12a}$ are (i) independently hydrogen or $C_{1-10}$ alkyl, or (ii) $R^{11}$ and $R^{12}$ taken together along with the nitrogen atom to which they are attached form a pyrrolidinyl, piperidinyl, azepinyl, or morpholine ring;

$R^{13}$ taken alone is selected from the group consisting of the side chain of a naturally occurring amino acids, optionally substituted phenyl and $C_{1-5}$ unbranched or branched alkyl;

$R^{14}$ taken alone is hydrogen, or $C_{1-6}$ alkyl; or, $R^{13}$ and $R^{14}$ taken together are $(CH_2)_3$;

X is a bond, O, S, NH;

n is 1 to 3;

o is 1 to 6; or, acid or base addition salts thereof.

2. A compound according to claim 1 wherein:

$R^3$ is hydrogen or fluoro;

$R^4$ is selected from the group consisting of hydrogen, chloro, fluoro and methyl;

$R^5$ is optionally substituted phenyl;

$R^6$ is $CH_2OH$, $CH_2OC(=O)XR^9$, $CH_2OCOCH(R^{13})NHR^{14}$ or $CH_2OP(=O)(OH)_2$;

$R^7$ and $R^8$ are independently selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen.

3. A compound according to claim 2 wherein $R^1$ is methyl, ethyl, trifluoromethyl or halogen.

4. A compound according to claim 3 wherein $R^5$ is monosubstituted phenyl.

5. A compound according to claim 3 wherein $R^5$ is 2,5-disubstituted phenyl.

6. A compound according to claim 3 wherein $R^5$ is 3,5-disubstituted phenyl.

7. A compound according to claim 3 wherein $R^5$ is 2,4-disubstituted phenyl.

8. A compound according to claim 3 wherein $R^5$ is 2,6-disubstituted phenyl.

9. A compound according to claim 2 wherein:

$R^1$ is methyl, ethyl, trifluoromethyl or halogen;

$R^2$ is hydrogen, halogen, methyl or ethyl;

$R^7$ is hydrogen, methyl or ethyl;

$R^8$ is selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen; and, X is a bond or —O—.

10. A compound according to claim 9 wherein $R^5$ is monosubstituted phenyl.

11. A compound according to claim 10 wherein $R^5$ is a monosubstituted phenyl and the substituent is selected from the group consisting of halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

12. A compound according to claim 11 wherein $R^1$ is selected from the group consisting of halogen, methyl and ethyl, $R^3$ and $R^7$ are hydrogen, $R^5$ is a monosubstituted phenyl and the substituent is selected from the group consisting of halogen, cyano, $C_{1-6}$ alkyl and $C_{1-6}$ haloalkyl, $R^8$ is selected from the group consisting of hydrogen, methyl and ethyl; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or O.

13. A compound according to claim 9 wherein $R^5$ is 2,5-disubstituted phenyl.

14. A compound according to claim 13 wherein $R^5$ is a 2,5-disubstituted phenyl and the substituents are independently selected from the group consisting of halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

15. A compound according to claim 14 wherein $R^1$ is selected from the group consisting of halogen, methyl, ethyl, $R^3$ and $R^7$ are hydrogen, $R^5$ is a 2,5-disubstituted phenyl and the substituent is selected from the group consisting of halogen, cyano, $C_{1-6}$ alkyl and $C_{1-6}$ haloalkyl and $R^8$ is selected from the group consisting of hydrogen, methyl and ethyl; $R^{11a}$ and $R^{12a}$ are (i) independently hydrogen or $C_{1-6}$ alkyl OR (ii) $R^{11a}$ and $R^{12a}$ taken with the nitrogen to which they are attached form a pyrrolidinyl, piperidinyl, azepinyl, or morpholine ring; and X is a bond or O.

16. A compound according to claim 9 wherein $R^5$ is 3,5-disubstituted phenyl.

17. A compound according to claim 16 wherein $R^5$ is a 3,5-disubstituted phenyl and the substituents are independently selected from the group consisting of halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

18. A compound according to claim 17 wherein $R^1$ is selected from the group consisting of halogen, methyl, ethyl, $R^3$ and $R^7$ are hydrogen, $R^5$ is a 3,5-disubstituted phenyl and the substituent is selected from the group consisting of halogen, cyano, $C_{1-6}$ alkyl $C_{3-8}$ cycloalkyl and $C_{1-6}$ haloalkyl and $R^8$ is selected from the group consisting of hydrogen, methyl and ethyl; $R^{11a}$ and $R^{12a}$ are (i) independently hydrogen or $C_{1-6}$ alkyl OR (ii) $R^{11a}$ and $R^{12a}$ taken with the nitrogen to which they are attached form a pyrrolidinyl, piperidinyl, azepinyl, or morpholine ring; and X is a bond or O.

19. A compound according to claim 18 with formula I wherein:

$R^5$ is

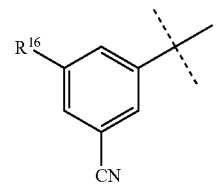

$R^1$ is selected from the group consisting of fluoro, chloro, bromo and methyl;

$R^2$, $R^3$ and $R^7$ are hydrogen;

$R^4$ is fluorine;

$R^6$ is $CH_2OH$, $CH_2OC(=O)XR^9$, $CH_2OCOCH(R^{13})NHR^{14}$ or $CH_2OP(=O)(OH)_2$;

$R^8$ is selected from the group consisting of hydrogen, methyl and ethyl;

$R^{16}$ is selected from the group consisting of $C_{1-6}$ alkyl, $C_{3-8}$ cycloalkyl, $C_{1-6}$ haloalkyl, halogen and cyano.

20. A compound according to claim 9 wherein $R^5$ is 2,4-disubstituted phenyl.

21. A compound according to claim 20 wherein $R^5$ is a 2,4-disubstituted phenyl and the substituents are independently selected from the group consisting of halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

22. A compound according to claim 21 wherein $R^1$ is selected from the group consisting of halogen, methyl, ethyl, $R^3$ and $R^7$ are hydrogen, $R^5$ is a 2,4-disubstituted phenyl and the substituent is selected from the group consisting of halogen, cyano, $C_{1-6}$ alkyl and $C_{1-6}$ haloalkyl and $R^8$ is selected from the group consisting of hydrogen, methyl and ethyl; $R^{11a}$ and $R^{12a}$ are (i) independently hydrogen or $C_{1-6}$ alkyl OR (ii) $R^{11a}$ and $R^{12a}$ taken with the nitrogen to which they are attached form a pyrrolidinyl, piperidinyl, azepinyl, or morpholine ring; and X is a bond or O.

23. A compound according to claim 9 wherein $R^5$ is 2,6-disubstituted phenyl.

24. A compound according to claim 23 wherein $R^5$ is a 2,6-disubstituted phenyl and the substituents are independently selected from the group consisting of halogen, cyano, $C_{1-6}$ alkyl, $C_{2-6}$ alkenyl, $C_{3-8}$ cycloalkyl, $C_{1-6}$ haloalkyl, $C_{1-6}$ alkoxy, $C_{1-6}$ alkylthio and $C_{1-6}$ haloalkoxy.

25. A compound according to claim 24 wherein $R^1$ is selected from the group consisting of halogen, methyl, ethyl, $R^3$ and $R^7$ are hydrogen, $R^5$ is a 2,6-disubstituted phenyl and the substituent is selected from the group consisting of halogen, cyano, $C_{1-6}$ alkyl and $C_{1-6}$ haloalkyl, $R^8$ is selected from the group consisting of hydrogen, methyl and ethyl; $R^{11a}$ and $R^{12a}$ are (i) independently hydrogen or $C_{1-6}$ alkyl OR (ii) $R^{11a}$ and $R^{12a}$ taken with the nitrogen to which they are attached form a pyrrolidinyl, piperidinyl, azepinyl, or morpholine ring; and, X is a bond or O.

26. A compound according to claim 9 wherein $R^5$ is a 2,3,5-trisubstituted phenyl.

27. A compound according to claim 1 wherein:

$R^3$ and $R^4$ are selected from the group consisting of hydrogen, chloro, fluoro, and methyl;

$R^5$ is optionally substituted pyridinyl, pyridine N-oxide, indole, indole N-oxide, quinoline, quinoline N-oxide, pyrimidinyl, pyrazinyl or pyrrolyl;

$R^6$ is $CH_2OH$, $CH_2OC(=O)XR^9$, $CH_2OCOCH(R^{13})NHR^{14}$ or $CH_2OP(=O)(OH)_2$;

$R^7$ and $R^8$ are selected from the group consisting of hydrogen, amino, $C_{1-6}$ alkylamino, $C_{1-6}$ dialkylamino, amino-$C_{1-3}$ alkyl, $C_{1-3}$ alkylamino-$C_{1-3}$ alkyl, $C_{1-3}$ dialkylamino-$C_{1-3}$ alkyl and $C_{1-6}$ alkyl optionally substituted with hydroxy, alkoxy, thiol, alkylthio or halogen;

X is a bond or O.

28. A compound according to claim 1 wherein the compound is selected from the group consisting of:
Succinic acid mono-{3-[4-chloro-3-(3,5-dicyano-phenoxy)-2-fluoro-benzyl]-5-methyl-6-oxo-6H-pyridazin-1-ylmethyl}ester,
Succinic acid mono-{3-[4-chloro-3-(3-chloro-5-cyano-phenoxy)-2-fluoro-benzyl]-5-methyl-6-oxo-6H-pyridazin-1-ylmethyl}ester,
Succinic acid mono-{3-[4-bromo-3-(3,5-dicyano-phenoxy)-2-fluoro-benzyl]-5-methyl-6-oxo-6H-pyridazin-1-ylmethyl}ester,
Succinic acid mono-{3-[4-bromo-3-(3-chloro-5-cyano-phenoxy)-2-fluoro-benzyl]-5-methyl-6-oxo-6H-pyridazin-1-ylmethyl}ester,
Succinic acid mono-{3-[4-chloro-3-(3-cyano-5-difluoromethyl-phenoxy)-2-fluoro-benzyl]-5-methyl-6-oxo-6H-pyridazin-1-ylmethyl}ester,
Succinic acid mono-{3-[4-chloro-3-(3-cyano-5-fluoro-phenoxy)-2-fluoro-benzyl]-6-oxo-6H-pyridazin-1-ylmethyl}ester,
Succinic acid mono-{3-[3-(3,5-dicyano-phenoxy)-4-ethyl-2-fluoro-benzyl]-5-methyl-6-oxo-6H-pyridazin-1-ylmethyl}ester,
Succinic acid mono-{3-[3-(3-chloro-5-cyano-phenoxy)-4-ethyl-2-fluoro-benzyl]-5-methyl-6-oxo-6H-pyridazin-1-ylmethyl}ester,
Succinic acid mono-{3-[3-(3-chloro-5-cyano-phenoxy)-2-fluoro-4-methyl-benzyl]-5-methyl-6-oxo-6H-pyridazin-1-ylmethyl}ester,
Succinic acid mono-{3-[3-(3,5-dicyano-phenoxy)-2-fluoro4-methyl-benzyl]-5-methyl-6-oxo-6-pyridazin-1-ylmethyl}ester, and,
Succinic acid mono-{3-[4-chloro-3-(3-cyano-5-difluoromethyl-phenoxy)-2-fluoro-benzyl]-6-oxo-6H-pyridazin-1-ylmethyl}ester.

29. A method for treating an HIV-1 infection in a host in need thereof comprising administering to a host in need thereof a therapeutically effective amount of a compound according to claim 1.

30. A method according to claim 29 wherein:
$R^1$ is methyl, ethyl, trifluoromethyl or halogen;
$R^2$ and $R^4$ are independently hydrogen, fluoro, chloro, methyl or ethyl;
$R^3$ is hydrogen or fluoro;
$R^5$ is optionally substituted phenyl;
$R^6$ is $CH_2OH$, $CH_2OC(=O)XR^9$, $CH_2OCOCH(R^{13})NHR^{14}$ or $CH_2OP(=O)(OH)_2$;
$R^7$ is hydrogen, methyl or ethyl; and,
X is a bond or —O—.

31. A method according to claim 30 comprising administering a compound of formula I wherein:

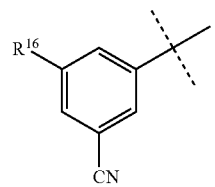

$R^1$ is selected from the group consisting of fluoro, chloro, bromo and methyl;
$R^2$, $R^3$ and $R^7$ are hydrogen;
$R^4$ is fluorine;
$R^6$ is $CH_2OH$, $CH_2OC(=O)XR^9$, $CH_2OCOCH(R^{13})NHR^{14}$ or $CH_2OP(=O)(OH)_2$;
$R^8$ is selected from the group consisting of hydrogen, methyl and ethyl;
$R^{16}$ is selected from the group consisting of $C_{1-6}$ alkyl, $C_{3-8}$ cycloalkyl, $C_{1-6}$ haloalkyl, halogen and cyano.

32. A method for inhibiting an HIV-1 reverse transcriptase comprising administering a compound according to claim 1.

33. A method according to claim 32 wherein said HIV-1 reverse transcriptase exhibits at least one mutation compared to wild type virus.

34. A method according to claim 33 wherein said strain of HIV-1 reverse transcriptase exhibits reduced susceptibility to efavirenz, nevirapine or delavirdine.

35. A pharmaceutical composition comprising a therapeutically effective quantity of a compound of according to claim 1 in admixture with at least one pharmaceutically acceptable carrier, excipient or diluent sufficient upon administration in a single or multiple dose regimen for treating diseases mediated by human immunodeficieny virus.

36. A process for preparing a compound of formula I wherein $R^6$ is $CH_2OH$, $CH_2OC(=O)XR^9$, $CH_2OCOCH(R^{13})NHR^{14}$; $R^{11a}$ and $R^{12a}$ are (i) independently hydrogen or $C_{1-6}$ alkyl or (ii) $R^{11a}$ and $R^{12a}$ taken with the nitrogen to which they are attached form a pyrrolidinyl, piperidinyl, azepinyl, or morpholine ring; X is a bond or O and $R^1$, $R^2$, $R^3$, $R^4$, $R^5$, $R^7$ and $R^8$ are as defined in claim 1 hereinabove,

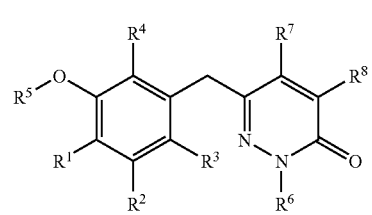

(I)

comprising the steps of:
(i) contacting a compound of formula I with formaldehyde or a formaldehyde equivalent, to produce a compound of formula I wherein $R^6$ is $CH_2OH$; optionally,
(ii) contacting the resulting hydroxymethyl compound with an activated carboxylic acid derivative, Y—C(=O)XR$^9$ or Y—C(=O)CH(R$^{13}$)NR$^{14}$R$^{15}$ wherein $R^9$, $R^{13}$, $R^{14}$ are as defined in claim 1 hereinabove, or heteroatom protected derivative thereof, $R^{15}$ is a nitrogen protecting group, and Y is a carboxylic acid activating group; and, optionally
(iii) removing any protecting groups to afford a compound of formula I wherein $R^6$ is $CH_2OH$, $CH_2OC(=O)XR^9$, $CH_2OCOCH(R^{13})NHR^{14}$.

* * * * *